United States Patent [19]

Hauck et al.

[11] 4,169,200

[45] Sep. 25, 1979

[54] SUBSTITUTED 3,6-DIHYDRO-1(2H)-PYRIDINYL-PROPANOLS

[75] Inventors: Frederic P. Hauck, Bridgewater; Rita T. Fox, Princeton; John R. Watrous, Pennington, all of N.J.

[73] Assignee: E. R. Squibb & Sons, Inc., Princeton, N.J.

[21] Appl. No.: 824,378

[22] Filed: Aug. 15, 1977

[51] Int. Cl.² .............. C07D 211/14; C07D 217/04; C07D 211/26; C07D 471/04
[52] U.S. Cl. .............................. 542/429; 546/101; 546/118; 546/147; 546/342; 546/270; 546/348
[58] Field of Search ................. 260/295 F; 546/101, 546/118, 147, 342, 270; 542/429

[56] References Cited

U.S. PATENT DOCUMENTS

| | | | |
|---|---|---|---|
| 3,894,031 | 7/1975 | Hauck et al. | 260/268 BC |
| 4,033,971 | 7/1977 | Hauck et al. | 260/295 F |
| 4,092,318 | 5/1978 | Hauck et al. | 546/206 |
| 4,101,723 | 7/1978 | Hauck et al. | 544/399 |
| 4,103,094 | 7/1978 | Hauck et al. | 546/342 |

OTHER PUBLICATIONS

Burger, Medicinal Chemistry, (1970), pp. 1019–1064.

*Primary Examiner*—David Wheeler
*Attorney, Agent, or Firm*—Lawrence S. Levinson; Donald J. Barrack

[57] ABSTRACT

Compounds having the formula

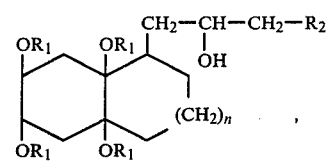

and the pharmaceutically acceptable salts thereof, wherein $R_1$ is alkanoyl; $R_2$ is

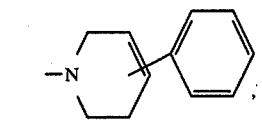
(i)

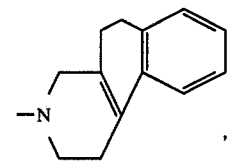

(ii)

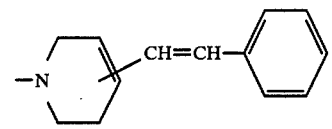

(iii)

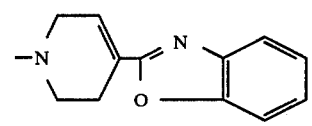

(iv)

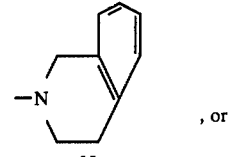

(v) , or

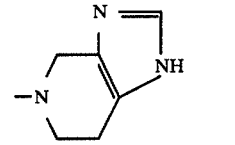
(vi) ;

and n is 0, 1 or 2; have useful hypotensive properties.

15 Claims, No Drawings

SUBSTITUTED 3,6-DIHYDRO-1(2H)-PYRIDINYLPROPANOLS

RELATED APPLICATION

Copending U.S. patent application Ser. No. 784,888, filed Apr. 5, 1977, now U.S. Pat. No. 4,101,723, issued July 18, 1978, by Hauck, Fox and Watrous discloses substituted piperazinopropanol hypotensive agents having the formula

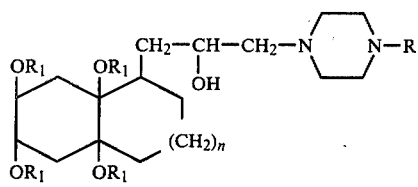

wherein $R_1$ is alkanoyl; R is aryl or pyridinyl; and n is 0, 1 or 2.

BACKGROUND OF THE INVENTION

Cyclitol derivatives having the formula

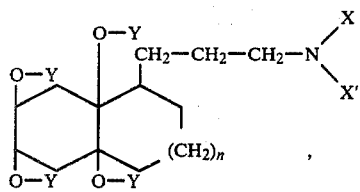

wherein Y is hydrogen or alkanoyl, the group -NXX' is a heterocyclic nitrogen containing group, and n is 0, 1 or 2 are encompassed by the disclosure of U.S. Pat. No. 3,894,031, issued July 8, 1975. Among the heterocyclic groups disclosed are piperidino, (lower alkyl)-piperidino, di(lower alkyl) piperidino, (lower alkoxy)-piperidino, aminomethylpiperidino, piperazino, (lower alkyl)piperazino, di(lower alkyl)piperazino, (lower alkoxy)piperazino, (hydroxy-lower alkyl)piperazino, (alkanoyloxy-lower alkyl)piperazino, (hydroxy-lower alkoxy-lower alkyl)piperazino, and (carbo-lower alkoxy)-piperazino. The treatment of hypertension is one of the utilities for the compounds disclosed by the patent.

Burger, *Medicinal Chemistry*, third edition (part II), John Wiley & Sons, Inc., New York, 1970, chapter 39, "Antihypertensive Agents", pgs. 1019–1064 discloses various classes of antihypertensive agents. Among the classes of compounds disclosed are veratrum alkaloids, the hypotensive activity of which may be largely attributable to the acylation of several hydroxyl functions of an alkamine. Other classes of antihypertensive agents disclosed by Burger include phenoxypropanolamines and phenethanolamines.

BRIEF DESCRIPTION OF THE INVENTION

Compounds having the formula

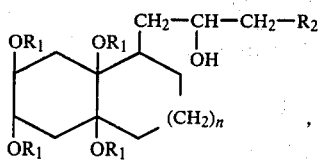

and the pharmaceutically acceptable salts thereof, have hypotensive activity. In formula I, and throughout the specification, the symbols are as defined below.

n is 0, 1 or 2;

$R_1$ is alkanoyl (acetyl is preferred);

$R_2$ is

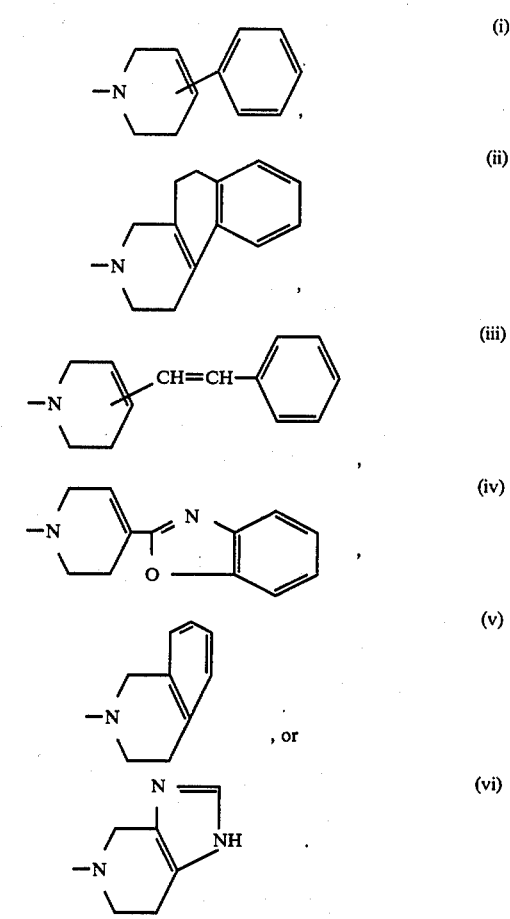

The term "alkanoyl", as used throughout the specification, refers to groups having the formula

wherein Y is alkyl having 1 to 6 carbon atoms.

DETAILED DESCRIPTION OF THE INVENTION

The substituted 3,6-dihydro-1(2H)-pyridinylpropanols of this invention can be prepared by reacting an oxirane compound having the formula

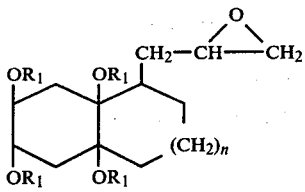

with a compound having the formula $R_2$—H.   III

Reaction conditions are not critical, but the reaction proceeds more rapidly when carried out with heating in an organic solvent, or mixture of organic solvents, e.g., a lower alkanol such as ethanol, or an aromatic hydrocarbon such as benzene in combination with a lower alkanol.

The oxirane compounds of formula II are readily obtained from a corresponding compound having the formula

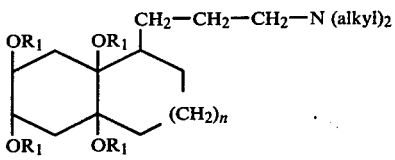

Compounds of formula IV are known; see, for example, U.S. Pat. No. 3,894,031, issued July 8, 1975. Oxidation of a compound of formula IV yields the corresponding N-oxide having the formula

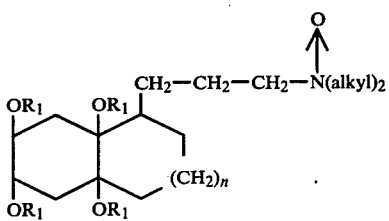

Exemplary of oxidizing agents which may be used are the peracids, e.g., m-chloroperbenzoic acid.

Vacuum pyrolysis of an N-oxide of formula V yields an olefin having the formula

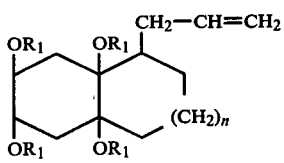

Oxidation of an olefin of formula VI yields the corresponding oxirane compound of formula II. Exemplary of oxidizing agents which may be used are the peracids, e.g., m-chloroperbenzoic acid.

The tetrahydropyridinyl derivatives of formula II are either known in the art, or can be prepared as described in the examples of this specification.

The compounds of formula I can be converted to their pharmaceutically acceptable acid-addition salts with both organic and inorganic acids using methods well known in the art. Exemplary salts are hydrohalides (e.g., hydrochloride and hydrobromide), nitrate, phosphate, borate, acetate, tartrate, methanesulfonate, benzenesulfonate, toluenesulfonate and the like.

Formula I includes all stereoisomers and mixtures thereof. Particular stereoisomers are prepared by utilizing as the starting material the compound of formula IV with the corresponding stereochemistry. The preferred stereoisomers are those in which the $OR_1$ groups are all axial. Particularly preferred are those compounds having the configuration

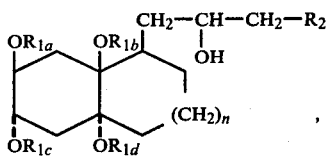

wherein the $OR_{1a}$ and $OR_{1c}$ groups are in the trans configuration as are the $OR_{1b}$ and $OR_{1d}$ groups.

The compounds of formula I show hypotensive properties in hypertensive rats and normotensive dogs. The compounds of this invention, and the pharmaceutically acceptable salts thereof, are useful as hypotensive agents in mammals, e.g., domestic animals such as dogs and cats. Daily doses of from 5 to 50 milligrams per kilogram of animal body weight, preferably about 5 to 25 milligrams per kilogram of animal body weight, can be administered orally or parenterally, in single or divided doses.

The compounds of this invention include indan derivatives having the formula

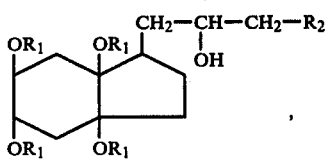

naphthalene derivatives having the formula

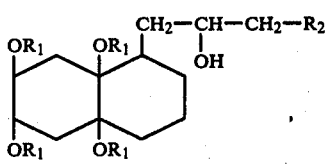

and benzocycloheptane derivatives having the formula

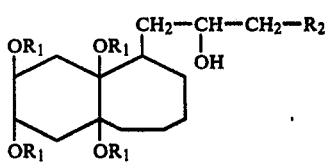

The naphthalene derivatives of formula IX are preferred.

The following examples are specific embodiments of this invention.

EXAMPLE 1

3,4a,5-cis-5-[3-(3,6-Dihydro-4-phenyl-1(2H)-pyridinyl)-2-hydroxypropyl]-decahydro-2,3;4a,8a-trans-naphthalenetetrol, tetraacetate ester A solution of 2.5 g of 3,4a,5-cis-decahydro-5-(oxiranylmethyl)-2,3;4a,8a-trans-naphthalenetetrol, tetraacetate ester (see copending U.S. patent application Ser. No. 784,888, filed Apr. 5, 1977) and 0.86 g of 4-phenyl-1,2,3,6-tetrahydropyridine is 20 ml benzene-50 ml absolute ethanol is stirred at 55°–57° C. for about 16 hours under a drying tube. The solution is evaporated in vacuo and the residue is crystallized from 30 ml of 1:2 ethyl acetate-ether to give 0.85 g of solid. A second crop yields 0.35 g of solid. Recrystallization from 2:1 ethyl acetate-ether yields 1.1 g of the title compound, melting point 193°–199° C.

EXAMPLE 2

Decahydro-5-[2-hydroxy-3-(1,4,5,6-tetrahydrobenz[f]isoquinolin-3(2H)-yl)propyl]-3,4a,5-cis-2,3;4a,8a-trans-naphthalenetetrol, tetraacetate ester 1,2,3,4,5,6-Hexahydrobenz[f]isoquinoline, monohydrochloride (1.0 g) is dissolved in 20 ml of water, layered over with ether and neutralized with aqueous ammonia. The organic phase is removed and the aqueous phase is reextracted with ether (two 20 ml portions). Organics are combined, dried, filtered and stripped in vacuo to yield 0.75 g of the free base, which is dissolved in 20 ml of benzene and 50 ml of absolute ethanol. 3,4a,5-cis-Decahydro-5-(oxiranylmethyl)-2,3;4a,8a-trans-naphthalenetetrol, tetraacetate ester (1.813 g) is added to the solution, and the resulting solution is heated to 50° C.±5° for 18 hours. Solvent is removed in vacuo, the residue is taken up in ether and the resulting powder is recrystallized from ethyl acetate to yield 1.17 g of the title compound.

EXAMPLE 3

3,4a,5-cis-Decahydro-5-[2-hydroxy-3-[4-(2-phenylethenyl)-3,6-dihydro-1(2H)-pyridinyl]propyl]-2,3;4a,8a-trans-naphthalenetetrol, tetraacetate ester (A)
1,2,3,6-Tetrahydro-4-(2-phenylethenyl)-1-(phenylmethyl)pyridine, monohydrochloride N-Benzylstyrylpyridinium bromide (59.0 g) is reduced by stirring in 750 ml of 50% aqueous methanol to which 30 g of sodium borohydride is added portionwise. Methanol is removed in vacuo, the resulting slurry is filtered and the solids are partitioned between water and chloroform. The aqueous layer is reextracted with chloroform. The chloroform extracts are combined, washed with aqueous sodium chloride, dried and stripped to yield 33.2 g of the title compound. Four grams of this product is dissolved in absolute ethanol, acidified with anhydrous hydrogen chloride in isopropanol, yielding 3.7 g of solid, which is recrystallized from methanol-isopropanol to yield 2.72 g of crystals, melting point 235°–240° C.

(B) 1,2,3,6-Tetrahydro-4-(2-phenylethenyl)pyridine

A solution of 46 g 1,2,3,6-tetrahydro-4-(2-phenethenyl)-1-(phenylmethyl)pyridine in 150 ml of toluene is treated with 30.1 g of phenyl chloroformate and heated at reflux for 12 hours. Solvent is removed in vacuo to yield 62.7 g of a solid. The above solid is heated to 130° C. with the aid of an oil bath and 50 g of powdered potassium hydroxide is added, portionwise. Heating is continued for 90 minutes, the mixture is cooled, taken up in 200 ml water and extracted with chloroform. Organics are combined, washed with aqueous sodium chloride, dried, filtered and stripped to yield 43 g of an oil which is taken up in ether, filtered and stripped to yield 33 g of oil. Twenty-eight grams of the oil is refluxed in 1 liter of hexane, the solvent is decanted from the oil, the oil is cooled to room temperature, filtered, then cooled in an ice box to yield a crystalline product. Due to the poor differential solubility, this process is repeated about eight times, yielding a total of 1.05 g of the free base.

(C)
3,4a,5-cis-Decahydro-5-[2-hydroxy-3-[4-(2-phenylethenyl)-3,6-dihydro-1(2H)-pyridinyl]propyl]-2,3;4a,8a-trans-naphthalenetetrol, tetraacetate ester 1,2,3,6-Tetrahydro-4-(2-phenylethenyl)pyridine (1.04 g) and 2.5 g of 3,4a,5-cis-decahydro-5-(oxiranylmethyl)-2,3;4a,8a-trans-naphthalenetetrol, tetraacetate ester are dissolved in 50 ml of absolute ethanol and 20 ml of benzene, and heated at 55° C.±5° for 15 hours. Solvent is evaporated in vacuo and the resulting gum crystallized from ether. Solids are collected yielding 1.35 g of brown solid which is taken up in ethyl acetate, decolorized with activated charcoal, filtered, hexane added and left standing. Resulting solids are collected and dried to yield 1.0 g of powder, melting point 183°–185° C.

EXAMPLE 4

3,4a,5-cis-5-[3-[4-(2,3-Dihydro-2-benzoxazolyl)-3,6-dihydro-1(2H)-pyridinyl]-2-hydroxypropyl]-decahydro-2,3;4a,8a-trans-naphthalenetetrol, tetraacetate ester (A) 2-(4-Pyridinyl)benzoxazole A mixture of 2-aminophenol (10.9 g), isonicotinic acid (12.3 g) and polyphosphoric acid (250 g) is heated under a nitrogen atmosphere at 210° C. for 3 hours. The mixture is then cooled to 160° C. and slowly poured into 1 liter of water. The mixture is cooled by adding ice and neutralized with 50% sodium hydroxide solution yielding 16.2 g of crude product. Crystallization from hexane yields 14.8 g of the title compound, melting point 129°–131° C.

(B) 4-(2-Benzoxazolyl)-1-(phenylmethyl)pyridinium chloride

A solution of 117.0 g of 2-(4-pyridinyl)benzoxazole and 95.0 g of benzyl chloride in 1 liter of a 9:1 mixture of n-propanol and dimethylsulfoxide is heated at reflux for 72 hours. The solvent mixture is then removed and the residue suspended in 100 ml of water. The crystalline product which separates is filtered, washed with acetone, and dried to give 76.6 g of product. Concentration of the mother liquors gives an additional 27.8 g of product, melting point 194°–196° C., dec. Recrystallization from water and drying in a vacuum at 100° C. for 5 hours raises the melting point to 216°–217° C., dec.

(C)
2-(1-Benzyl-1,2,3,6-tetrahydro-4-pyridinyl)benzoxazole

To a stirred solution of 16.6 g of 4-(2-benzoxazolyl)-1-(phenylmethyl)pyridinium chloride in 1 liter of a 1:1 mixture of alcohol and water is added a solution of 2.84 g of sodium borohydride at a rate that maintains the temperature of the mixture at 30°–35° C. The reaction mixture is acidified with hydrochloric acid, concentrated to one-half volume and the crystals filtered to give 8.7 g of the hydrochloride salt of the title compound, melting point 227°–228° C., dec.

The mother liquors are made alkaline with solid sodium bicarbonate, extracted with chloroform and the extract concentrated to give a gummy residue. Recrystallization of this material from absolute alcohol gives 2.1 g of the title compound, melting point 129°–130° C.

(D)
4-(2-Benzoxazolyl)-3,6-dihydro-1(2H)-pyridinecarboxylic acid, 2,2,2-trichloroethyl ester To a vigorously stirred solution of 109.1 g of 2-(1-benzyl-1,2,3,6-tetrahydro-4-pyridinyl)benzoxazole in 1 liter of dry toluene is added dropwise 96.4 g of 2,2,2-trichloroethyl chloroformate during 2 hours and the mixture is heated at reflux for 1.5 hours. The reaction mixture is then cooled, extracted with 250 ml of cold 10% hydrochloric acid, with 250 ml of cold 10% aqueous sodium hydroxide solution, and with an equal volume of water, dried (anhydrous magnesium sulfate), and concentrated. The oily residue is then further concentrated from an oil bath maintained at 50° C. under a vacuum of 0.2 mm of Hg to remove the remaining benzyl chloride.

The viscous oil is dissolved in 500 ml of boiling absolute ethanol and cooled to give, after filtration and drying, 56.9 g of crystalline product, melting point 134°–135° C. The mother liquors give, after concentration to one-half volume and cooling an additional 11.0 g of product identical with that above.

(E) 2-(1,2,3,6-Tetrahydro-4-pyridinyl)benzoxazole

To a solution of 52.6 g of 4-(2-benzoxazolyl)-3,6-dihydro-1(2H)-pyridinecarboxylic acid, 2,2,2-trichloroethyl ester in 1250 ml of glacial acetic acid is gradually added 92.5 g of zinc dust and the reaction mixture stirred at room temperature under nitrogen for 6 hours. The reaction mixture is filtered and concentrated on the rotary evaporator to give a viscous gum. This material is suspended in 500 ml of water, the pH adjusted to 2–3, and the suspension extracted with 500 ml of ether in two portions. These are combined, dried and concentrated to give 11.32 g of unreacted starting material.

The separated turbid, aqueous phase is filtered, cooled, made strongly alkaline, and extracted three times with 250 ml portions of chloroform. The combined extracts are dried and concentrated to give 6.0 g of crystals, melting point 136°–138° C.

(F)
3,4a,5-cis-5-[3-[4-(2,3-Dihydro-2-benzoxazolyl)-3,6-dihydro-1(2H)-pyridinyl]-2-hydroxypropyl]-decahydro-2,3;4a,8a-trans-naphthalenetetrol, tetraacetate ester Three grams of 3,4a,5-cis-decahydro-5-(oxiranylmethyl)-2,3;4a,8a-trans-naphthalenetetrol, tetraacetate ester is dissolved in 50 ml of absolute ethanol and 20 ml of benzene. To this is added 1.34 g of 2-(1,2,3,6-tetrahydro-4-pyridinyl)benzoxazole and the resulting solution is heated to 55° C.±5° for 16 hours. Solvent is stripped in vacuo and the resulting gum is taken up in ether. The ether solution is filtered, diluted with hexane and left standing. Solids are collected to yield 3 g of solid which is recrystallized from ethyl acetate and hexane to yield 1.6 g of the title compound, melting point 204°–210° C., dec.

EXAMPLE 5
3,4a,5-cis-Decahydro-5-[2-hydroxy-3-(1,2,3,4-tetrahydro-2-isoquinolinyl)propyl]-2,3;4a,8a-trans-naphthalenetetrol, tetraacetate ester A solution of 3.0 g of 3,4a,5-cis-decahydro-5-(oxiranylmethyl)-2,3;4a,8a-trans-naphthalenetetrol, tetraacetate ester and 0.94 g of 1,2,3,4-tetrahydroisoquinoline in ethanol-benzene (50:20) is warmed in a 55° C. bath for about 16 hours. The solution is evaporated in vacuo to give 4 g of solid. Two recrystallizations from ethyl acetate/ether/hexane yield 1.9 g of the title compound, melting point 185°–195° C.

EXAMPLE 6
3,4a,5-cis-Decahydro-5-[2-hydroxy-3-(4,5,6,7-tetrahydro-1H-imidazo[4,5-c]pyridin-5-yl)propyl]-2,3;4a,8a-trans-naphthalenetetrol To a solution of 0.55 g of sodium hydroxide in 30 ml of absolute ethanol is added 1.35 g of 4,5,6,7-tetrahydro-1H-imidazo[4,5-c]pyridine, hydrochloride. After stirring for about 5 minutes a solution of 3.0 g of 3,4a,5-cis-decahydro-5-(oxiranylmethyl)-2,3;4a,8a-trans-naphthalenetetrol, tetraacetate ester in 30:50 ethanol:benzene is added and the solution is stirred for about 16 hours at 40°–45° C. The mixture is filtered and the filtrate is evaporated in vacuo to give 3.8 g of foam. The foam is dissolved in 50:20 ethanol:benzene and stirred for 24 hours at 55°–58° C. The solvent is removed in vacuo and the residue is dissolved in ethyl acetate, heated with activated charcoal and filtered. After diluting with a small amount of ether and storing at −15° C. for 3 days, 1.3 g of solid is obtained. Recrystallization from ethyl acetate (trace methanol) yields 1.0 g of the title compound, melting point 214°–216° C.

EXAMPLES 7–8

Following the procedure of Example 1, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
| --- | --- |
| 3a,5-cis-3a,7a;5,6-trans-hexahydro-1-(oxiranylmethyl)-1H-indene-3a,5,6,7a-tetrol, tetraacetate ester (see United States patent application serial no. 784,888, filed April 5, 1977) | 3a,5-cis-3a,7a;5,6-trans-hexahydro-1-[3-(3,6-dihydro-4-phenyl-1(2H)-pyridinyl)-2-hydroxypropyl]-1H-indene-3a,5,6,7a-tetrol, tetraacetate ester |
| 3,4a,5-cis-hexahydro-5-(oxiranylmethyl)-2,3;4a,9a-trans-benzocycloheptanetetrol-tetraacetate ester (see United States patent application serial no. 784,888, filed April 5, 1977) | 3,4a-cis-hexahydro-5-[3-(3,6-dihydro-4-phenyl-1(2H)-pyridinyl)-2-hydroxypropyl]-2,3;4a,9a-trans-benzocycloheptanetetrol, tetraacetate ester |

EXAMPLES 9–10

Following the procedure of Example 2, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 3a,5-cis-3a,7a;5,6-trans-hexahydro-1-(oxiranylmethyl)-1H-indene, 3a,5,6,7a-tetrol, tetraacetate ester | 3a,5-cis-3a,7a;5,6-trans-hexahydro-1-[2-hydroxy-3-(1,4,5,6-tetrahydrobenz[f]isoquinolin-3(2H)-yl)propyl]-1H-indene-3a,5,6,7a-tetrol, tetraacetate ester |
| 3,4a,5-cis-hexahydro-5-(oxiranylmethyl)-2,3;4a,9a-trans-benzocycloheptane-tetrol, tetraacetate ester | 3,4a-cis-hexahydro-5-[2-hydroxy-3-(1,4,5,6-tetra-hydrobenz[f]isoquinolin-3(2H)-yl)propyl]-2,3;4a,9a-trans-benzocycloheptanetetrol, tetraacetate ester |

EXAMPLES 11-12

Following the procedure of Example 3, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 3a,5-cis-3a,7a;5,6-trans-hexahydro-1-(oxiranylmethyl)-1H-indene-3a,5,6,7a-tetrol, tetraacetate ester | 3a,5-cis-3a,7a;5,6-trans-hexahydro-1-[2-hydroxy-3-[4-(1-phenylethenyl)-3,6-dihydro-1(2H)-pyridinyl]propyl]-1H-indene-3a,5,6,-7a-tetrol, tetraacetate ester |
| 3,4a,5-cis-hexahydro-5-(oxiranylmethyl)-2,3;4a,9a-trans-benzocycloheptane-tetrol, tetraacetate ester | 3,4a-cis-hexahydro-5-[2-hydroxy-3-[4-(1-phenyl-ethenyl)-3,6-dihydro-1(2H)-pyridinyl]propyl]-2,3;4a,9a-trans-benzocyclo-heptanetetrol, tetra-acetate ester |

EXAMPLES 13-14

Following the procedure of Example 4, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 3a,5-cis-3a,7a;5,6-trans-hexahydro-1-(oxiranylmethyl)-1H-indene-3a,5,6,7a-tetrol, tetraacetate ester | 3a,5-cis-3a,7a;5,6-trans-hexahydro-1-[3-[4-(2,3-dihydro-2-benzoxazolyl)-3,6-dihydro-1(2H)-pyridinyl]2-hydroxypropyl]-1H-indene-3a,5,6,7a-tetrol, tetra-acetate ester |
| 3,4a,5-cis-hexahydro-5-(oxiranylmethyl)-2,3;4a,9a-trans-benzocycloheptane-tetrol, tetraacetate ester | 3,4a-cis-hexahydro-5-[3-[4-(2,3-dihydro-2-benzoxazolyl)3,6-dihydro-1(2H)-pyridinyl]2-hydroxypropyl]-2,3;4a,9a-trans-benzocyclohexane-tetrol, tetraacetate ester |

EXAMPLES 15-16

Following the procedure of Example 5, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 3a,5-cis-3a,7a;5,6-trans-hexahydro-1-(oxiranylmethyl)-1H-indene-3a,5,6,7a-tetrol, tetraacetate ester | 3a,5-cis-3a,7a;5,6-trans-hexahydro-1-[2-hydroxy-3-(1,2,3,4-tetrahydro-2-isoquinolinyl)propyl]-1H-indene-3a,5,6,7a-tetrol, tetraacetate ester |
| 3,4a,5-cis-hexahydro-5-(oxiranylmethyl)-2,3;4a,9a-trans-benzocycloheptane-tetrol, tetraacetate ester | 3,4a-cis-hexahydro-5-[2-hydroxy-3-(1,2,3,4-tetra-hydro-2-isoquinolinyl)-propyl]-2,3;4a,9a-trans-benzocycloheptanetetrol, tetraacetate ester |

EXAMPLES 17-18

Following the procedure of Example 6, but substituting the compound listed in column I for 3,4a,5-cis-decahydro-5-(oxiranylmethyl)-2,3;4a,8a-trans-naphthalenetetrol, tetraacetate ester, yields the compound listed in column II.

| Column I | Column II |
|---|---|
| 3a,5-cis-3a,7a;5,7-trans-hexahydro-1-(oxiranylmethyl)-1H-indene-3a,5,6,7a-tetrol, tetraacetate ester | 3a,5-cis-3a,7a;5,6-trans-hexahydro-1-[2-hydroxy-3-(4,5,6,7-tetrahydro-1H-imidazo[4,5-c]pyridin-5-yl)propyl]-1H-indene-3a,-5,6,7a-tetrol, tetra-acetate ester |
| 3,4a,5-cis-hexahydro-5-(oxiranylmethyl)-2,3;4a,9a-trans-benzocycloheptanetetrol, tetraacetate ester | 3,4a-cis-hexahydro-5-[2-hydroxy-3-(4,5,6,7-tetra-hydro-1H-imidazo[4,5-c]-pyridin-5-yl)propyl]-2,3;-4a,9a-trans-benzocyclo-heptanetetrol, tetra-acetate ester |

What is claimed is:
1. A compound having the formula

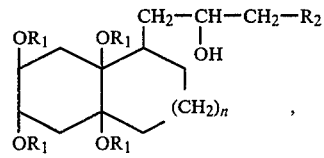

or a pharmaceutically acceptable salt thereof, wherein n is 0, 1 or 2; $R_1$ is alkanoyl having 2 to 7 carbon atoms; and $R_2$ is

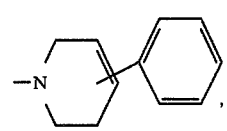

(i)

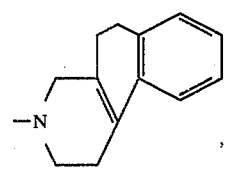

(ii)

-continued

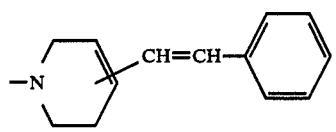
(iii)

,

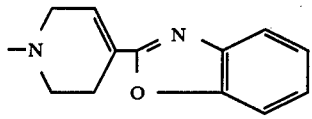
(iv)

,

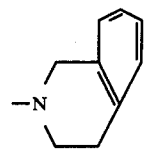
, or

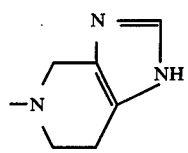

2. A compound in accordance with claim 1 wherein n is 1.

3. A compound in accordance with claim 2 wherein R₁ is acetyl.

4. A compound in accordance with claim 3 wherein R₂ is

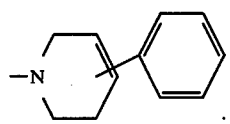

5. A compound in accordance with claim 3 wherein R₂ is

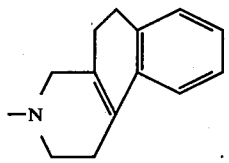

6. A compound in accordance with claim 3 wherein R₂ is

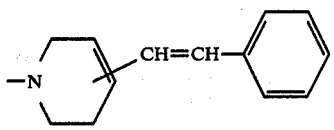
(v)

7. A compound in accordance with claim 3 wherein R₂ is

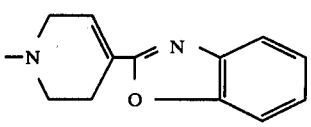
(vi)

8. A compound in accordance with claim 3 wherein R₂ is

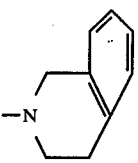

9. A compound in accordance with claim 3 wherein R₂ is

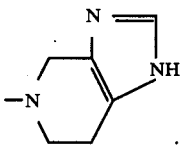

10. The compound in accordance with claim 4 having the name 3,4a,5-cis-5-[3-(3,6-dihydro-4-phenyl-1(2H)-pyridinyl)-2-hydroxypropyl]-decahydro-2,3;4a,8a-trans-naphthalenetetrol, tetraacetate ester.

11. The compound in accordance with claim 5 having the name decahydro-5-[2-hydroxy-3-(1,4,5,6-tetrahydrobenz[f]isoquinolin-3(2H)-yl)propyl]-3,4a,5-cis-2,3;4a,8a-trans-naphthalenetetrol, tetraacetate ester.

12. The compound in accordance with claim 6 having the name 3,4a,5-cis-decahydro-5-[2-hydroxy-3-[4-(2-phenylethenyl)-3,6-dihydro-1(2H)-pyridinyl]propyl]-2,3;4a,8a-trans-naphthalenetetrol, tetraacetate ester.

13. The compound in accordance with claim 7 having the name 3,4a,5-cis-5-[3-[4-(2,3-dihydro-2-benzoxazolyl)-3,6-dihydro-1(2H)-pyridinyl]-2-hydroxypropyl]-decahydro-2,3;4a,8a-trans-naphthalenetetrol, tetraacetate ester.

14. The compound in accordance with claim 8 having the name 3,4a,5-cis-decahydro-5-[2-hydroxy-3-(1,2,3,4-tetrahydro-2-isoquinolinyl)propyl]-2,3;4a,8a-trans-naphthalenetetrol, tetraacetate ester.

15. The compound in accordance with claim 9 having the name 3,4a,5-cis-decahydro-5-[2-hydroxy-3-(4,5,6,7-tetrahydro-1H-imidazo[4,5-c]pyridin-5-yl)propyl]-2,3;4a,8a-trans-naphthalenetetrol.

* * * * *